Figure 1:
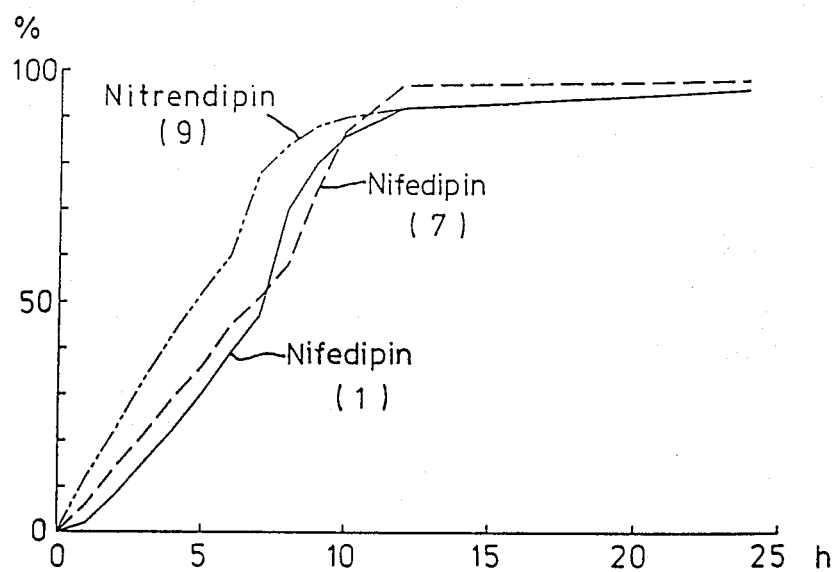

United States Patent [19]

Ohm et al.

[11] Patent Number: 4,892,741

[45] Date of Patent: Jan. 9, 1990

[54] PRESS COATED DHP TABLETS

[75] Inventors: Andreas Ohm, Neuss; Helmut Luchtenberg, Niederkassel; Shinji Maegata, Oharanaka; Wolfgang Opitz, Overath, all of Fed. Rep. of Germany

[73] Assignee: Bayer Aktiengesellschaft, Leverkusen, Fed. Rep. of Germany

[21] Appl. No.: 204,056

[22] Filed: Jun. 8, 1988

[30] Foreign Application Priority Data

Jun. 24, 1987 [DE] Fed. Rep. of Germany ....... 3720751

[51] Int. Cl.$^4$ .............................................. A61K 9/36
[52] U.S. Cl. ..................................... 424/479; 424/474; 424/480; 424/482
[58] Field of Search ............... 424/482, 480, 479, 494, 424/474

[56] References Cited

U.S. PATENT DOCUMENTS

| | | | |
|---|---|---|---|
| 3,184,386 | 5/1965 | Stephenson | 424/479 X |
| 3,558,768 | 1/1971 | Klippel | 424/480 X |
| 4,654,206 | 3/1987 | Okuda et al. | 424/480 |
| 4,765,990 | 8/1988 | Sigimoto et al. | 424/494 |
| 4,803,081 | 2/1989 | Falk et al. | 424/480 X |

FOREIGN PATENT DOCUMENTS

| | | |
|---|---|---|
| 2331375 | 6/1977 | France . |
| 1144915 | 3/1969 | United Kingdom . |
| 2123291 | 2/1984 | United Kingdom ................ 424/480 |

OTHER PUBLICATIONS

104:174662y, Kimura et al., "Controlled-Release Pharmaceuticals Containing Nifedipine . . . ", Chem. Ab. V. 104, May 1986, p. 391.

T. Wagner, "Die Praxis der Mantel-und Mehrschichttablette", Pharmazeutische Industrie, v. 24 (9/1962) pp. 417-422.

Primary Examiner—Thurman K. Page
Attorney, Agent, or Firm—Sprung Horn Kramer & Woods

[57] ABSTRACT

The invention relates to solid pharmaceutical preparations which have a long-lasting action and are for dihydropyridines in the form of a press coated tablet, and a process for their preparation.

12 Claims, 1 Drawing Sheet

PRESS COATED DHP TABLETS

Active compounds from the dihydropyridine class of substances and their use as cardiac and circulatory agents have already been disclosed (compare Brit. Pat. 1,173,862, Brit. pat. 1,358,951, US-Pat. 4,256,749, German Offenlegungsschrift 3,311,003 and U.S. Pat. No. 4,264,611). Difficulties frequently appear in the galenical preparation of these potent active compounds, in that the substances possess only a very low solubility, are frequently light-sensitive and their absorbability in biological systems frequently leads to problems. Numerous experiments have been undertaken to produce galenical preparations which improve the bioavailability of these potent active compounds. Thus, for example, some active compounds have been dissolved in specific organic solvent systems and filled into gelatine capsules in order to ensure a rapid and effective commencement of action (compare Brit. Pat. 1,362,627). The conversion of dihydropyridines such as nifedipine into co-precipitates or into "solid solutions" has also been attempted using water-soluble polymers, in order to improve the bioavailability (compare Brit. Pat. 1,579,818).

For the treatment of illnesses which must be treated over relatively long periods of time, such as, for example, hypertension, it is desirable to keep the frequency of administration of medicaments as low as possible. This is not only more aggreeable for the patient, but also increases the safety of the treatment by diminishing the disadvantages of irregular administration and leads to a uniform active compound concentration/time profile in the body. The risk of under- or overdosing is thereby minimized at the same time.

Both for the physician and also for the patient, there is a demand, for example for the continuous therapy or circulatory diseases, to have available the highly active dihydropyridines in a form in which a once daily application suffices for treatment of the disease. Medicament preparations having delayed release of active compound (retard forms) have already been described for dihydropyridines. Thus, for example, the production of a slow-release preparation has been attempted by specific particle size distribution of the crystalline active compound or by a selected specific surface area of the crystals of the active compound (compare German Offenlegungsschrift 3,033,919). Furthermore, specific tablet preparations have been proposed which, according to the principle of the osmotic pump, release the active compound from the interior of a tablet which is provided with a semi-permeable coating layer through a given opening over a relatively long period of time and thus to achieve a retard effect (compare U.S. Pat. No. 3,916,899).

The previously known forms of preparation having retarded release of active compound, in particular those for dihydropyridines, exhibit a number of disadvantages. Their retard action is, for example, only limited to a few hours in some forms, so that the patient must, as a rule, administer them two or more times daily as before. After a few hours, the rate of release of the active compound decreases markedly, so that the blood level can also drop beneath the necessary efficacy limit.

In German Offenlegungsschrift 2,651,176, pellets having controlled release of active compound are described. The formulations described there differ fundamentally from the coated tablets according to the invention, since these pellets can only be obtained in complex processes by continuous application of many layers, whereas the tablet according to the invention is prepared by simple compression. An additional substantial difference is that the spherical pellets according to this Offenlegungsschrift even when they are produced in tablet dimensions, show a terminally decreasing release rate as opposed to the stepwise terminally increasing release rate of the coated tablets according to the invention. In the embodiment examples described there, only readily soluble active compounds are employed and all the examples describe the preparation of the pellet layers using lipophilic retarding agents. The use according to the invention of hydrophilic polymers, in particular hydroxypropyl-cellulose, cannot be carried out practically by the embodiment examples of this Offenlegungsschrift.

In the abovementioned osmotic system, local irritation of the tissue can occur in the stomach or gastrointestinal tract, depending on the capsule filling employed, owing to excessive concentration. Furthermore, a flattening of the release curve in the terminal region is also to be observed in the case of this osmotic retardation principle, which should ensure a linear course of release over a relatively long period of time. Due to the nature of the osmotic system, some of the active compound remains in the medicament form and is thus not available for the desired absorption. An additional disadvantage of this system is the delayed setting in of active compound release after administration, which in some cases only begins after about 2 hours. In addition, the production of this medicament form is very expensive, since organic solvents must be employed in the preparation process here and the coating layer of each tablet must be perforated separately with the aid of a laser beam.

It has now been found that solid medicament preparations which have a long-lasting action in the form of a coated tablet and which contain a sparingly soluble dihydropyridine active compound of the general formula I

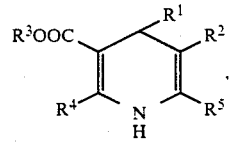

in which
$R^1$ represents a phenyl radical which is substituted by one or two identical or different substituents from the group comprising nitro, halogen and trifluoromethyl, or represents a radical from the group comprising

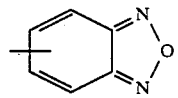

and 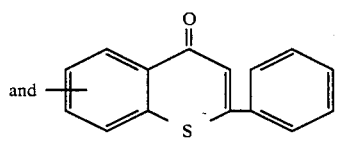

$R^2$ represents a nitro group or the radical $COOR_6$, in which $R_6$ denotes alkyl having 1 to 10 C atoms which is optionally substituted by alkoxy having 1 to 4 C atoms or by one or more halogens, or in which $R^2$, together with $R^5$, represents the lactone group $-CO-O-CH_2$, $R^3$ represents alkyl having 1 to 10 C atoms, which is optionally substituted by alkoxy having 1 to 4 C atoms or by one of more fluorine atoms and $R^4$ and $R^5$ are identical or different and in each case represent alkyl having 1 to 4 C atoms, which is optionally substituted by hydroxyl, where the coated tablet (a) consists of a core which contains at least one of the abovementioned dihydropyridines in rapid-release form and (b) consists of a coating around the core, this coating containing at least one of the abovementioned dihydropyridines in slow-release form, show a surprisingly long-lasting efficacy.

Coated tablets may be preferably mentioned which contain 5% to 50%, preferably 10% to 40%, of the total dihydropyridine active compound in the core and which contain 50% to 95%, in particular 60% to 90%, of the total dihydropyridine active compound in the coating.

Particularly preferred active compounds which may be mentioned are nifedipine, nitrendipine, nimodipine and nisoldipine.

According to the type of active compound, the coated tablets according to the invention preferably contain 1 to 200 mg in total, in particular 10 to 150 mg, of at least one active compound from the dihydropyridine class.

The rapid-release core of the coated tablet preferably contains the active compound in amorphous form or in finely grounded or micronized crystalline form. When using crystalline active compound, the release rate is preferably influenced by the addition of auxiliaries with good water solubility and by alteration of the particle size distribution of the active compound.

Tablet cores having rapid release are preferably those cores which release 75% of the dihydropyridine active compound in one hour, preferably in 30 minutes, under the following conditions: 4 liters of 0,1N hydrochloric acid and 0,1–0,5% of weight of surfactant e.g. TWEEN 80 or sodiumlaurylsulphate; 37° C.; 100 Rpm; USP-Paddle method.

If the rapid-release core contains amorphous dihydropyridine, the latter is preferably dissolved in an organic solvent together with water-soluble polymers such as polyvinylpyrrolidone, methylcellulose, hydroxypropyl-cellulose or hydroxypropylmethylcellulose. It is expedient here to employ 2 to 10 parts by weight, in particular 3 to 8 parts by weight, of the water-soluble polymers to 1 part by weight of dihydropyridine and to prepare suitable co-precipitates from this.

If the rapid-release core contains dihydropyridines in crystalline form, dihydropyridine crystals having a maximum mean particle size of about 25 μm, in particular a maximum mean particle size of about 15 μm, are preferably employed. The particle size is determined by the Cilas method (lit.: A. Buerkholz et al, Part. Charact. 1, 1984, 153–160, "Laser defraction spectrometers/experience in particle size analysis").

When using crystalline dihydropyridine in the core, the addition of readily water-soluble auxiliaries such as, for example, lactose is expedient. Likewise, the release rate can be accelerated by the use of disintegrants, such as, for example, crosslinked polyvinylpyrrolidone (PVP), or surface-active substances, such as, for example, sodium lauryl sulphate.

The preparation of this rapid-release core takes place by customary methods (compare German Offenlegungsschrift 3,415,128 and German Offenlegungsschrift 3,142,853 or Brit. Pat. 1,579,818).

The granules for the coat of the tablet contain 10 to 99%, preferably 20 to 90%, of the total coating weight of hydrophilic gel-forming polymers.

Suitable hydrophilic gel-forming polymers are, for example, modified starch or cellulose-like substances such as, for example, methylcellulose, hydroxypropylmethyl-cellulose, hydroxypropylcellulose and sodium carboxymethyl-cellulose. Hydroxypropylcellulose (HPC) may be mentioned as being particularly preferred (compare: Hagers Handbuch der pharmazeutischen Praxis (Hager's Handbook of Pharmaceutical Practice), volume 7, part B, (1977) 130–141).

Various types of HPC can be used according to the invention, in each case differing in their viscosity, for example HPC-L (low viscosity of about 6–10 mPa.s), HPC-M (medium viscosity of about 150 mPa.s) and HPC-H (high viscosity of about 1000–4000 mPa.s). The release rate can be controlled through the different viscosity grades, the release rate increasing when lower viscosity grades are employed and slowing when using higher viscosity types.

In some cases, it is expedient to apply some of the active compound as the initial dose in the form of an outer layer of the coated tablet using the known techniques and auxiliaries.

Customary known galenical measures, such as, for example, the coating of the core with a gastric juice-resistant layer, the use of flavorings and aromas and lubricants and customary auxiliaries which are familiar to the galenical expert, can of course also be employed and used in the press coated tablets according to the invention.

It should be expressly pointed out that the coated tablet according to the invention differs from the previously known coated tablets due to the fact that the coating contains the active compound in slow-release form and the core contains the active compound in rapid-release form.

Multi-layer tablets based on casein matrices, which contain two or three layers which in each case can in turn contain active compounds (compare U.S. Pat. No. 3,184,386), have already been described in the prior art. The tablets described there contain a rapid-release preparation in the outer coating, the core primarily having the function of not allowing the surface of the outer active compound-containing layer relevant for the release to become too small. This patent specification contains no indication, however, that the core of the preparation contains a sparely soluble active compound in rapid-release form. On the contrary, both the central coat and also the core are described in the examples as slow-release-forms of highly soluble active compounds.

Coated tablets which contain active compounds in slow-release form both in the core and in the coating are also described in U.S. Pat. No. 3,558,768. The release rates according to this US patent specification may be different, but the specification refers only to slow-release forms.

Through the principle of the coated tablet according to the invention, the hitherto customary disadvantages of normal retard tablets and also of previously known multilayer or coated tablets or of preparation forms which depend upon the osmotic principle are avoided. In particular, the situation where the release rate of the active compound becomes smaller and smaller towards the end of the dissolution of the tablets and the plasma levels thus sink is avoided. The decreasing release rate of normal retard tablets due to a reduction in the volume of the tablet is more than compensated for by the rapid-release action of the core of the press coated tablet according to the invention. Complete release of the active compound is achieved at the same time, in contrast to osmotic systems.

The formulation according to the invention differs from all previously known retardation principles for solid medicament forms through the acceleraed release rate in the terminal region.

Any reduced absorption of the administered medicament substance in deeper intestinal sections, for example limited by hindrance of diffusion, may thus be better equalized. Further advantages which may be mentioned are the rapid influx of the active compound after administration with the avoidance of a retardation phase and also the simple preparation technology. A further advantage of the inventive formulations is, that they are specially useful for those drugs, which show a higher resorption in the lower parts of the gastro intestinal tracts e.g. in the colon. This may lead to an increase of the bioavailability of those drugs.

Inventive composition can be manufactured by the following procedure:

(A) Core:

In accordance with usual techniques the active substance and the other ingredients are mixed and granulated by adding an aqueous solution of binders, e.g. in a planatory mixer or in a high speed mixer or by fluidized bed granulation. The granulate is dried, preferably in a fluidized bed dryer. The dried granulate is sieved and mixed with magnesiumstearate and afterwards pressed to tablets. Alternatively the manufacture of the core can be made by direct compression of the ingredients or by roller compaction plus compression. Optionally the coure can be coated by usual methods, preferably in a coating pan or by other usual means.

Granules for the coat:

The granulate is produced preferably in a fluidized bed granulator by spraying an aqueous suspension containing the active substance and a binder on the solid ingredients, the obtained granules are dried, sieved and mixed with a lubricant, e.g. magnesiumstearate.

The production of the granules can also be made by other usual techniques.

Press coating:

The press coating of the core is carried out on usual press coaters (e.g. machines of the company Kilian or Manesty).

Optionally the press coated tablets can be film coated with usual laquers. In certain cases it may be recommendable to incorporate a small amount of the active substance into this film coating layer, the maximum amount of the active substance in the film coating layer should be 20% of the total amount of the active substance.

With regard to the long existing requirement for medicament preparation forms having a long-lasting action, it is more than surprising that hitherto nobody has described or produced the coated tablets according to the invention having a rapid-release core which are simple to produce and very effective. Through the present invention, the patient is placed in the position of only having to take the medicament once daily, which in continuous therapy, in particular, represents a safer and more agreeable type of treatment.

The curves in FIG. 1 show for several examples according to the invention the principle of the coat of the tablet which is slowly released over several hours and the core which is released rapidly.

ILLUSTRATIVE EMBODIMENTS

Example 1

(A) Core 50 g of crystalline nifedipine (mean particle size 5 μm) are mixed with 388 g of lactose and 150 g of corn starch, and the mixture is granulated in a paste of 10 g of starch and 140 g of hot water and then dried. The granules are sieved and mixed with 50 g of microcrystalline cellulose and 2 g of magnesium stearate. This mixture is compressed to 65 mg weight tablets having a diameter of 6 mm. The cores are coated for resistance to gastric juice using an organic solution of hydroxypropyl-methylcellulose phthalate. The coated tablets weigh 72 mg.

(B) Granules for the coat 250 g of nifedipine are mixed with 400 g of lactose, 16 g of colloidal silica, 700 g of type M hydroxy-propylcellulose, 1747 g of type L hydroxypropylcellulose (HPC) and 320 g of citric acid, and the mixture is granulated in a fluidized bed granulator with a solution of 20 g of type L hydroxypropyl-cellulose. The dried and sieved granules are mixed with 27 g of magnesium stearate.

These granules and the cores described under (A) are pressed to 420 mg weight press coated tablets having a diameter of 10 mm in a press coater. The tablets are then coated using an aqueous dispersion of hydroxypropyl-methylcellulose, polyethylene glycol, titanium dioxide and iron oxide red.

Example 2

(A) Core
Preparation as in Example 1.

(B) Granules for the coat: 400 g of lactose are mixed with 17 g of colloidal silica, 2196 g of type L hydroxy-propyl-cellulose, 250 g of type M hydroxypropylcellulose and 320 g of citric acid, and the mixture is granulated with an aqueous suspension of 250 g nifedipine and 20 g of type L hydroxypropyl-cellulose in a fluidized bed granulator. The dried granules are sieved and mixed with 27 g of magnesium stearate.

These granules and the cores described under (A) are pressed to 420 mg weight press coated tablets having a diameter of 10 mm in a press coater. The tablets are then coated using an aqueous dispersion of hydroxypropyl-methylcellulose, polyethylene glycol, titanium dioxide and iron oxide red.

Example 3

(A) Core 50 g of crystalline nifedipine (mean particle size 8 μm) are mixed with 291 g of lactose and 162.5 g of corn starch, and the mixture is granulated using a paste of 7.5 g of corn starch in 100 g of hot water. The granules are dried, sieved and then mixed with 1.5 g of magnesium stearate and 37.5 g of microcrystalline cellulose. This mixture is compressed to 55 mg weight cores having a diameter of 5.5 mm.

(B) Granules for the coat 400 g of lactose are mixed with 17 g of colloidal silica, 1105 g of type L HPC, 443 g of type M HPC and 202 g of citric acid, and the mixture is granulated using an aqueous suspension consisting of 250 g of nifedipine and 16 g of type L HPC. The granules are dried and sieved and mixed with 17 g of magnesium stearate.

Press coated tablets having a weight of 300 mg and a diameter of 9 mm are produced from these granules and the cores. The tablets are then coated as in Example 1.

Example 4

(A) Core

Preparation as in Example 3.

The cores are coated for resistance to gastric juice using an organic solution of hydroxypropylmethyl-cellulose phthalate. The coated tablets weigh 60 mg.

(B) Granules for the coat 250 g of nifedipine are mixed with 400 g of lactose, 17 g of colloidal silica, 1155 g of type L HPC, 343 g of type M HPC and 202 g of citric acid, and the mixture is granulated using an aqueous solution of 16 g of type L HPC. The granules are dried, sieved and mixed with 17 g of magnesium stearate.

Press Coated tablets having a weight of 300 mg and a diameter of 9 mm are prepared from these granules and the cores. The tablets are then coated as in Example 1.

Example 5

(A) Core 250 g of crosslinked polyvinylpyrrolidone and 197 g of microcrystalline cellulose are mixed and granulated using a solution of 30 g of nifedipine and 150 g of polyvinylpyrrolidone 25 in 350 g of acetone. The granules are dried and sieved and pressed with 3 g of magnesium stearate. This mixture is pressed to 65 mg weight tablets having a diameter of 6 mm. The cores are coated using an organic solution of hydroxypropylmethylcellulose phthalate. The coated cores weigh 72 mg.

(B) Granules for the coat

The granules are prepared analogously to Example 1. The additional processing is as in Example 1.

Example 6

(A) Core

Preparation as in Example 3.

(B) Granules for the coat 200 g of nifedipine are mixed with 350 g of lactose, 17 g of colloidal silica, 1105 g of type L HPC, 443 g of type M HPC and 202 g of citric acid, and the mixture is granulated using an aqueous solution of 16 g of type L HPC. The granules are dried and sieved and mixed with 12 g of magnesium stearate.

Press Coated tablets having a weight of 290 mg are pressed from these granules and the cores.

5 mg of nifedipine per tablet are coated onto these tablets from an aqueous dispersion containing hydroxypropylmethylcellulose and polyethylene glycol. These tablets are then covered with a light protecting coating analogously to Example 1.

Example 7

(A) Core 50 g of crystalline nifedipine (mean particle size 10 μm) are mixed with 600 g of lactose and 228 g of corn starch, and the mixture is granulated using a paste of 20 g of starch and 320 g of water and then dried. The granules are sieved and mixed with 2 g of magnesium stearate, and the mixture is pressed to 90 mg weight tablets having a diameter of 7 mm. The cores are coated using an organic solution of hydroxypropylmethylcellulose phthalate. The coated cores weigh 97 mg.

(B) Granules for the coat 250 g of nifedipine are mixed with 400 g of lactose and 16 g of colloidal silica, and the mixture is granulated using a solution of 16 g of type L hydroxypropylcellulose in water. The dried and sieved granules are mixed with 900 g of type M hydroxypropylcellulose, 2387 g of type L hydroxypropylcellulose, 400 g of citric acid and 61 g of magnesium stearate.

These granules and the cores described under (A) are pressed to 540 mg weight tablets having a diameter of 11 mm in a press coater. The tablets are then coated using an aqueous dispersion of hydroxypropylmethylcellulose, polyethylene glycol, titanium dioxide and iron oxide red.

Example 8

(A) Core 100 g of crystalline nifedipine (mean particle size 4 μm) are mixed with 241 g of lactose and 162.5 g of corn starch, and the mixture is granulated with a paste of 7.5 g of corn starch in 100 g of water. The dried granules are sieved and mixed with 1.5 g of magnesium stearate and 37.5 g of Avicel and this mixture is pressed to 55 mg weight tablets having a diameter of 5.5 mm.

(B) Granules for the coat 500 g of nifedipine are mixed with 335 g of lactose and 16 g of colloidal silica, and the mixture is granulated using a solution of 33 g of type L hydroxypropylcellulose in water. The dried granules are sieved and mixed with 443 g of type M hydroxypropylcellulose, 1105 g of type L hydroxypropylcellulose and 18 g of magnesium stearate.

These granules and the cores described under (A) are pressed to 300 mg weight tablets having a diameter of 9 mm in a press coater. The tablets are then coated using an aqueous dispersion of hydroxy-propylmethylcellulose, polyethylene glycol, titanium dioxide and iron oxide red.

Examples 9 and 10 were prepared in an analogous manner.

Example 9

Core:

| | |
|---|---:|
| nitrendipine mean particle size 6 μm | 5.0 mg |
| corn starch | 27.8 mg |
| microcrystalline cellulose | 20.0 mg |
| lactose | 21.49 mg | are mixed and then granulated with:

| | |
|---|---:|
| polyvinylpyrrolidone 25 | 5.0 mg |
| sodium lauryl sulphate | 0.5 mg |
| FD + C blue lake No. 2 | 0.01 mg | in aqueous suspension by means of customary granulation processes

| after drying, magnesium stearate | 0.2 mg |
|---|---| is admixed. The mixture is pressed to cores in a tablet press: weight: 80 mg, size: φ6 mm

| Granules for the coat: | |
|---|---|
| type L hydroxypropylcellulose | 210.0 mg |
| type M hydroxypropylcellulose | 82.0 mg |
| citric acid | 146.0 mg | are mixed and granulated with an aqueous suspension of

| nitrendipine (mean particle size 5 μm) | 25.0 mg |
|---|---|
| hydroxypropylcellulose type L | 2.0 mg |
| after drying admixing of magnesium stearate | 5.0 mg |

Press Coated tablets are prepared with the aid of a press coater Total weight: 550 mg Size: φ10 mm

Example 10

Core:

| nitrendipine mean particle size 5 μm | 5.0 mg |
|---|---|
| microcrystalline cellulose | 17.5 mg |
| lactose | 6.4 mg |
| corn starch | 7.5 mg |
| mixing and granulation with | |
| polyvinylpyrrolidone 25 | 3.0 mg |
| sodium lauryl sulphate | 0.5 mg | in aqueous solution by means of customary granulation processes after drying,

| magnesium stearate | 0.1 mg |
|---|---| is admixed and the mixture is pressed to cores in a tablet press: weight: 40 mg, size: φ5.5 mm Granules for the coat:

| micronized nitrendipine | 25.0 mg |
|---|---|
| type L hydroxypropylcellulose | 221.0 mg | are mixed and granulated (if desired a part of the hydroxypropylcellulose can be removed for processing in the granulation liquid)

| admixing of magnesium stearate | 7.0 mg |
|---|---|

Press Coated tablets are prepared with the aid of a press coater. Total weight: 293 mg Size: 9 mm

Example 11

Core:

| nitrendipine (mean particle size 10 μm) | 2.5 mg |
|---|---|
| corn starch | 23.0 mg |
| microcrystalline cellulose | 20.0 mg |
| lactose | 21.5 mg |

| -continued | |
|---|---|
| Plasdone XL | 7.3 mg | are granulated using an aqueous solution of:

| polyvinylpyrrolidone 25 | 5 mg |
|---|---|
| sodium lauryl sulphate | 0.5 mg | after drying,

| magnesium stearate | 0.2 mg |
|---|---| is admixed and the mixture pressed to cores in a tablet press. Weight: 80 mg, size: 6 mm Granules for the coat:

| micronized nisoldipine | 12.5 mg |
|---|---|
| type L hydroxypropylcellulose | 212 mg |
| type M hydroxypropylcellulose | 82 mg |
| lactose | 158.5 mg | are mixed and granulated with water admixing of

| magnesium stearate | 12 mg |
|---|---|

Press Coated tablets are prepared with the aid of a press coater Total weight: 557 mg Size: 10 mm

Example 12

(A) Core

The preparation is as in Example 8, 200 g of nimodipine and 141 g of lactose now being employed instead of 100 g of nifedipine and 241 g of lactose.

(B) Granules for the coat

Preparation by analogy with Example 8, 600 g of nimodipine and 235 g of lactose now being employed instead of 500 g of nifedipine and 335 g of lactose.

The aqueous coating is likewise analogous to Example 8, but without the use of red iron oxide.

Example 13

(A) Core

The preparation is analogous to Example 8, 50 g of nifedipine, 150 g of nisoldipine and 141 g of lactose now being employed instead of 100 g of nifedipine and 241 g of lactose.

(B) Granules for the coat

The preparation is analogous to Example 8, 200 g of nifedipine and nisoldipine now being employed instead of 500 g of nifedipine.

At the same time, 518 g of HPC-M and 1030 l g of HPC-L are now used instead of 443 g of HPC-M and 1105 g of HPC-L.

Example 14

Core:

| nitrendipine of mean particle size 5 μm | 8.0 mg |
|---|---|
| microcrystalline cellulose | 12.0 mg |
| lactose | 4.0 mg |
| Plasdone XL | 15.0 mg | mixing and granulation with

| | |
|---|---|
| polyvinylpyrrolidone 25 | 2.0 mg |
| sodium lauryl sulphate | 0.8 mg | in aqueous solution by means of customary granulation processes after drying,

| | |
|---|---|
| magnesium stearate | 0.2 mg | is admixed and the mixture is pressed to cores in a tablet press: weight: 42 mg, size: 5 mm
Granules for the coat:

| | |
|---|---|
| micronized nitrendipine | 32.0 mg |
| type L hydroxypropylcellulose | 77.0 mg |
| type M hydroxypropylcellulose | 77.0 mg |
| lactose | 92.5 mg | are mixed and granulated (if desired a part of the hydroxypropylcellulose can be removed for processing in the granulation liquid)

| | |
|---|---|
| admixing of magnesium stearate | 1.5 mg |

Press Coated tablets are prepared with the aid of a press coater. Total weight: 322.0 mg; size: 9 mm Example 15

A. Core:
50 g Nifedipine (mean particle size 5 μm) are mixed with 170 g lactose and 173,5 g corn starch. This mixture is granulated with an aqueous paste of 5 g corn starch. After drying and sieving 1,5 g magnesium stearate, 50 g plasdone XL and 50 g Avicel are added. The granules are compressed to tablets with a size of 5 mm and a weight of 50 mg.

B. granules for the coat
1101 g hydroxypropylcellulose type L, 755 g hydroxypropylcellulose type M, 341 g lactose and 16 g of colloidal silica are mixed. This mixture is granulated using an aqueous suspension of 250 g nifedipine and 20 g HPC type L. The granules are dried and sieved and mixed with 17 g of magnesium stearate. Press coated tablets having a weight of 300 mg and a diameter of 9 mm are pressed from these granules and the cores.

C. Coating
The tablets are then coated with an aqueous suspension of hydroxypropylmethylcellulose, polyethylene glycol, titanium dioxide and iron oxide red in order to give light protection.

Example 16

A. Core
100 g nifedipine (mean particle size 5 μm) are mixed with 160 g lactose, 148,8 corn starch. This mixture is granulated with an aqueous paste of 5 g corn starch. After drying and sieving 1,3 g magnesium stearate, 50 g plasdone XL and 34,9 g Avicel are added. The granules are compressed to tablets with a size of 5 mm and a weight of 50 mg.

B. granules for the coat
1010 g hydroxypropylcellulose type L, 628 g hydroxypropylcellulose type M, 289 g lactose and 16 g of colloidal silica are mixed. This mixture is granulated using an aqueous suspension of 500 g nifedipine and 40 g HPC type L. The granules are dried and sieved and mixed with 17 g of magnesium stearate. Press coated tablets having a weight of 300 mg and a diameter of 9 mm are pressed from these granules and the cores.

C. Coating
The tablets are then coated with an aqueous suspension of hydroxypropylmethylcellulose, polyethylene glycol, titanium dioxide and iron oxide red in order to give light protection.

Example 17

A. Core
150 g nifedipine (mean particle size 5 μm) are mixed with 130 g lactose, 124 g corn starch. This mixture is granulated with an aqueous paste of 5 g corn starch. After drying and sieving 1 g magnesium stearate, 50 g plasdone XL and 40 g Avicel are added. The granules are compressed to tablets with a size of 5 mm and a weight of 50 mg.

B. granules for the coat
780 g hydroxypropylcellulose type L, 588 g hydroxypropylcellulose type M, 289 g lactose and 16 g of colloidal silica are mixed. This mixture is granulated using an aqueous suspension of 750 g nifedipine and 60 g HPC type L. The granules are dried and sieved and mixed with 17 g of magnesium stearate. Press coated tablets having a weight of 300 mg and a diameter of 9 mm are pressed from these granules and the cores.

C. Coating
The tablets are then coated with an aqueous suspension of hydroxypropylmethylcellulose, polyethylene glycol, titanium dioxide and iron oxide red in order to give light protection.

Example 18

A. Core
8 g nitrendipine (mean particle size 5 μm) are mixed with 4 g lactose, 15 g crosslinked PVPP and 12,3 g microcrystalline cellulose. This mixture is granulated with an aqueous solution of 1,8 g PVP and 0,8 g sodium laurylsulfate. After drying and sieving 0,1 g magnesium stearate are added. The granules are compressed to tablets with a size of 5 mm and a weight of 42 mg.

B. granules for the coat
104,5 g hydroxypropylcellulose type L, 40 g hydroxypropylcellulose type M and 88,5 g lactose are mixed. This mixture is granulated using an aqueous suspension of 32 g nitrendipine and 1,5 g HPC type L. The granules are dried and sieved and mixed with 1,5 g of magnesium stearate. Press coated tablets having a weight of 310 mg and a diameter of 9 mm are pressed from these granules and the cores.

C. Coating
The tablets are then coated with an aqueous suspension of hydroxypropylmethylcellulose, polyethylene glycol and titanium dioxide.

Example 19

A. Core
20 g nitrendipine (mean particle size 5 μm) are mixed with 15 g crosslinked PVP and 7,2 g microcrystalline cellulose. This mixture is granulated with an aqueous solution of 1,8 g PVP and 0,9 g sodium lauryl sulfate. After drying and sieving 0,1 g magnesium stearate are added. The granules are compressed to tablets with a size of 5 mm and a weight of 45 mg.

B. granule for the coat 144.5 g hydroxypropylcellulose type L and 97,5 g lactose are mixed. This mixture is granulated using an aqueous suspension of 20 g nitrendipine and 1,5 g HPC type L. The granules are dried and sieved and mixed with 1,5 g of magnesium stearate. Press coated tablets having a weight of 310 mg and a diameter of 9 mm are pressed from these granules and the cores.

C. Coating

The tablets are then coated with an aqueous suspension of hydroxypropylmethylcellulose, polyethylene glycol and titanium dioxide.

Example 20

A. Core 4 g nisoldipine (mean particle size 5 μm) are mixed with 8 g lactose, 15 g crosslinked PVPP and 12,3 g microcrystalline cellulose. This mixture is granulated with an aqueous solution of 1,8 g PVP and 0,8 g sodium laurylsulfate. After drying and sieving 0,1 g magnesium stearate are added. The granules are compressed to tablets with a size of 5 mm and a weight of 42 mg.

B. granule for the coat 46,5 g hydroxypropylcellulose type L, 100 g hydroxypropylcellulose type M and 103 g lactose are mixed. This mixture is granulated using an aqueous suspension of 16 g nisoldipine and 1,5 g HPC type L. The granules are dried and sieved and mixed with 1 g of magnesium stearate. Press coated tablets having a weight of 310 mg and a diameter of 9 mm are pressed from these granules and the cores.

C. Coating

The tablets are then coated with an aqueous suspension of hydroxypropylmethylcellulose, polyethylene glycol, titanium dioxide and iron oxide red in order to give light protection.

Example 21

A. Core 4 g nisoldipine (mean particle size 5 μm) are mixed with 8 g lactose, 15 g crosslinked PVPP and 12,3 g microcrystalline cellulose. This mixture is granulated with an aqueous solution of 1,8 g PVP and 0,8 g sodium laurylsulfate. After drying and sieving 0,1 g magnesium stearate are added. The granules are compressed to tablets with a size of 5 mm and a weight of 42 mg.

B. granule for the coat 92,5 g hydroxypropylcellulose type L, 54 g hydroxypropylcellulose type M and 103 g lactose are mixed. This mixture is granulated using an aqueous suspension of 16 g nisoldipine and 1,5 g HPC type L. The granules are dried and sieved and mixed with 1 g of magnesium stearate. Press coated tablets having a weight of 310 mg and a diameter of 9 mm are pressed from these granules and the cores.

C. Coating

The tablets are then coated with an aqueous suspension of hydroxypropylcellulose, polyethylene glycol, titanium dioxide and iron oxide red in order to give light protection.

Example 22

A. Core 4 g nisoldipine (mean particle size 5 μm) are mixed with 8 g lactose, 15 g crosslinked PVP and 12,3 g microcrystalline cellulose. This mixture is granulated with an aqueous solution of 1,8 g PVP and 0,8 g sodium laurylsulfate. After drying and sieving 0,1 g magnesium stearate are added. The granules are compressed to tablets with a size of 5 mm and a weight of 42 mg.

B. granule for the coat 175 g hydroxypropylcellulose type M and 74,5 g lactose are mixed. This mixture is granulated using an aqueous suspension of 16 g nisoldipine and 1,5 g HPC type L. The granules are dried and sieved and mixed with 1 g of magnesium stearate. Press coated tablets having a weight of 310 mg and a diameter of 9 mm are pressed from these granules and the cores.

C. Coating

The tablets are then coated with an aqueous suspension of hydroxypropylmethylcellulose, polyethylene glycol, titanium dioxide and iron oxide red in order to give light protection.

It will be understood that the specification and examples are illustrative but not limitative of the present invention and that other embodiments within the spirit and scope of the invention will suggest themselves to those skilled in the art.

We claim:

1. A solid medicament preparation having a long-lasting action in the form of a press coated tablet which contains a sparingly soluble dihydropyridine, the press coated tablet comprising
   (a) a core which contains a dihydropyridine in rapid-release form, and
   (b) a coat around the core, the coat containing a dihydropyridine in slow-release form.

2. A press coated tablet according to claim 1, wherein the dihydropyridine is of the formula

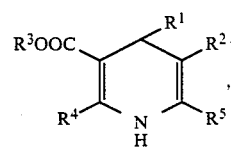

in which $R^1$ represents a phenyl radical which is substituted by one or two identical or different substituents from the group comprising nitro, halogen and trifluoromethyl, or represents a radical from the group comprising

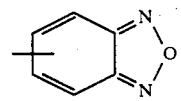

and

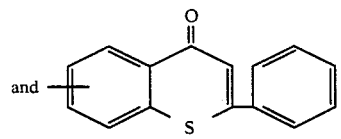

$R^2$ represents a nitro group or the radical $COOR_6$, in which $R_6$ denotes alkyl having 1 to 10 C atoms which is optionally substituted by alkoxy having 1 to 4 C atoms or by one or more halogens, or in which $R^2$, together with $R^5$, represents the lactone group —CO—O—CH$_2$, $R^3$ represents alkyl having 1 to 10 C atoms, which is optionally substituted by alkoxy having 1 to 4 C atoms or by one or more fluorine atoms and $R^4$ and $R^5$ are identical or different and in each case represent alkyl having 1 to 4 C atoms, which is optionally substituted by hydroxyl.

3. A press coated tablet according to claim 1, containing about 5 to 50% of the total dihydropyridine in the core and about 95 to 50% of the total dihydropyridine in the coat.

4. A press coated tablet according to claim 1, containing about 10 to 40% of the total dihydropyridine in the core and about 90 to 60% of the total dihydropyridine in the coat.

5. A press coated tablet according to claim 1, wherein the core contains the dihydropyridine in amorphous form or in crystalline form having a maximum mean particle size of 25 μm.

6. A press coated tablet according to claim 1, wherein about 10 to 99% of the total coat weight is a hydrophilic gel-forming polymer.

7. A press coated tablet according to claim 6, wherein the coat contains methylcellulose, hydroxypropylmethylcellulose, hydroxypropylcellulose and/or sodium carboxymethylcellulose as the hydrophilic gel-forming polymer.

8. A press coated tablet according to claim 7, wherein the coat contains hydroxypropylcellulose as the hydrophilic gel-forming polymer.

9. A press coated tablet according to claim 1, wherein the dihydropyridine comprises at least one compound selected from the group consisting of nifedipine, nitrendipine, nimodipine and nisoldipine.

10. A press coated tablet according to claim 1, wherein the core contains the dihydropyridine in crystalline form and further contains at least one of a readily water-soluble auxiliary, disintegrant and wetting agent.

11. A press coated tablet according to claim 1, wherein the coating is itself coated with a layer of dihydropyridine in rapid-release form.

12. A process for manufacturing solid medicament preparations having a long lasting action containing a sparingly soluble dihydropyridine in form of a press coated tablet comprising:

(a) a core which contains a dihydropyridine in rapid-release form, and (b) a coat around the core, the coat containing a dihydropyridine in slow-release form, the core having been produced by mixing the active substance and a filler, granulating this mixture by adding an aqueous solution of binder, drying and sieving the granulate, adding a lubricant and pressing to form the core, or forming the core by direct compression or by roller compaction plus compression, producing the granule for the coat by spraying an aqueous suspension containing the active substance and a binder on the solid ingredients, drying and sieving, mixing with a lubricant, press coating the granules for the coat upon the core, and optionally film coating the obtained press coated tablet with lacquers which optionally contain a small amount of the active substance up to a maximum of 20% of the total amount of the active substance in the whole composition.

* * * * *